United States Patent [19]

Akashi et al.

[11] Patent Number: 4,713,474
[45] Date of Patent: Dec. 15, 1987

[54] ALKANEDICARBOXYLIC DIESTER COMPOUNDS

[75] Inventors: Hiroyuki Akashi, Chikujo; Takeshi Inoue; Shoichi Horie, both of Nakatsu, all of Japan

[73] Assignee: Yoshitomi Pharmaceutical Industries, Ltd., Osaka, Japan

[21] Appl. No.: 887,452

[22] PCT Filed: Nov. 16, 1985

[86] PCT No.: PCT/JP85/00641
  § 371 Date: Jul. 3, 1986
  § 102(e) Date: Jul. 3, 1986

[87] PCT Pub. No.: WO86/03193
  PCT Pub. Date: Jun. 5, 1986

[30] Foreign Application Priority Data

Nov. 20, 1984 [JP] Japan .................. 59-245672
May 21, 1985 [JP] Japan .................. 60-109867

[51] Int. Cl.⁴ .......................... C07C 69/76
[52] U.S. Cl. ........................ 560/66; 514/533
[58] Field of Search ........................ 560/66

[56] References Cited

FOREIGN PATENT DOCUMENTS 1547223 11/1968 France .
55-27350 2/1980 Japan .

OTHER PUBLICATIONS

C. A., 93(6):47827k, 1980.
C. A., 97(16):128211g, 1982.
C. A., 93(24):221373w, 1980.
Chemical Abstracts, vol. 84(9), 58848h, (1976).

*Primary Examiner*—Paul J. Killos
*Attorney, Agent, or Firm*—Wenderoth, Lind & Ponack

[57] ABSTRACT

An alkanedicarboxylic diester compound represented by the formula:

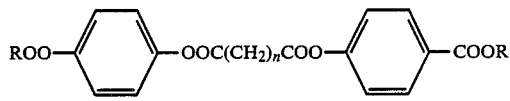

wherein n is an integer of 0–8 and R is a benzyl group. The compounds have a repellency action to vermin and a plasticization action to thermoplastic polymers, and are useful as a pesticide or plasticizer.

1 Claim, No Drawings

ALKANEDICARBOXYLIC DIESTER COMPOUNDS

TECHNICAL FIELD AND DISCLOSURE OF THE INVENTON

This invention relates to novel alkanedicarboxylic diester compounds represented by the formula:

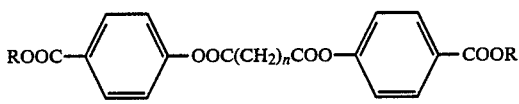

wherein n is an integer of 0~8 and R is benzyl group or alkyl group having 3~8 carbon atoms.

The compounds are useful as pest-repellants and plasticizers.

The present inventors have prepared various types of new compounds in order to develop compounds having pest-repellancy action and increasing plasticization efficiency to a thermoplastic polymer, and then have discovered such compounds.

This invention has been accomplished based on these findings.

This invention relates to alkanedicarboxylic diester compounds represented by the formula:

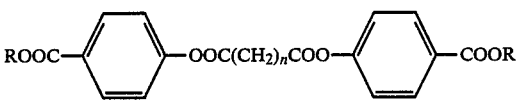

wherein n is an integer of 0~8 and R is benzyl group or alkyl group having 3~8 carbon atoms.

The compounds of this invention can be readily prepared by reacting, for example, alkanedicarboxylic acid dichloride represented by the formula:

wherein n is an integer of 0~8, with alkyl p-hydroxybenzoate or benzyl p-hydroxybenzoate in a suitable solvent such as toluene, benzene, chloroform, dichloroethane in the presence of an amine such as triethylamine, pyridine, dimethylaniline.

The resulting compound is purified by a conventional method such as column chromatography, recrystallization by methanol, DMF, acetonitrile, etc.

In using the compound of this invention as a pest-repellant, it is mixed with a conventional carrier for a pest-repellant, kneaded in a synthetic resin, e.g. polyvinyl chloride or any other material intended for repellency of vermin, coated or impregnated with a brush or by spraying.

The amount in which the compound is used varies depending on the mode of use and is such that is enough to exhibit a repellency action to vermin. For example, 0.5 to 10 parts by weight of it may be compounded to 1 part by weight of a carrier.

Further, the compounds of this invention impart a superior plasticization efficiency to a thermoplastic polymer and increase its suppleness, elasticity, plasticity with a low volatility. Hence they are useful as a plasticizer for polymers.

EXAMPLE 1

Into a 300 ml four-neck flask equipped with a dropping funnel, a calcium chloride tube and a thermometer are charged 16.6 g of ethyl p-hydroxybenzoate, 7.9 g of pyridine and 150 ml of ethylether. A solution of 9.2 g of adipic acid dichloride in 20 ml of ethylether is added dropwise to the mixture with stirring while retaining the mixture at 0°–5° C. over 30 minutes. After addition, the mixture is further allowed to react at 0°–5° C. for 1 hour. Thereafter, the ethylether from the resulting reaction product is distilled and subsequently, recrystallized from methanol to give di(p-ethyloxycarbonylphenyl) adipate melting at 82°–83° C. as white crystals.

EXAMPLE 2

A similar procedure to Example 1 is carried out by using 16.6 g of ethyl p-hydroxybenzoate and 8.5 g of glutaric acid dichloride to yield di(p-ethyloxycarbonylphenyl)glutarate, m.p. 81°–82° C., as white crystals.

EXAMPLE 3

A similar procedure to Example 1 is carried out by using 7.8 g of propyl p-hydroxybenzoate and 18 g of succinic acid dichloride to yield di(p-propyloxycarbonylphenyl)succinate, m.p 122°–123.5° C., as white crystals.

EXAMPLE 4

A similar procedure to Example 1 is carried out by using 18 g of propyl p-hydroxybenzoate and 8.5 g of glutaric acid dichloride to yield di(p-propyloxycarbonylphenyl)glutarate, m.p. 74°–75° C., as white crystals.

EXAMPLE 5

A similar procedure to Example 1 is carried out by using 15.2 g of methyl p-hydroxybenzoate and 7.8 g of succinic dichloride to yield di(p-methyloxycarbonylphenyl)succinate, m.p. 189.5°–190° C., as white crystals.

EXAMPLE 6

A similar procedure to Example 1 is carried out by using 15.2 g of methyl p-hydroxybenzoate and 12 g of sebacic acid dichloride to yield di(p-methyloxycarbonylphenyl)sebacate, m.p. 109.5°–110.5° C., as white crystals.

EXAMPLE 7

A similar procedure to Example 1 is carried out by using 16.7 g of benzyl p-hydroxybenzoate and 16.7 g of sebacic acid dichloride to yield di(p-benzyloxycarbonylphenyl)sebacate, m.p. 62.5°–63° C., as white crystals.

EXAMPLE 8

A similar procedure to Example 1 is carried out by using 32 g of p-hydroxybenzoic acid and 12.8 g of adipic acid dichloride to yield di(p-benzyloxycarbonylphenyl)adipate, m.p. 93°–93.5° C., as white crystals.

EXAMPLE 9

A similar procedure to Example 1 is carried out by using 22.8 g of benzyl p-hydroxybenzoate and 8.45 g of glutaric acid dichloride to yield di(p-benzyloxycarbonylphenyl)glutarate, m.p. 93°–94° C., as white crystals.

EXAMPLE 10

A similar procedure to Example 1 is carried out by using 22.8 g of benzyl p-hydroxybenzoate and 7.7 g of succinic acid dichloride to yield di(p-benzyloxycarbonylphenyl)succinate, m.p. 106°–107° C., as white crystals.

EXAMPLE 11

A similar procedure to Example 1 is carried out by using 22.8 g of benzyl p-hydroxybenzoate and 7.1 g of malonic acid dichloride to yield di(p-benzyloxycarbonylphenyl)malonate, m.p. 78°–80° C., as white crystals.

EXAMPLE 12

A similar procedure to Example 1 is carried out by using 22.8 g of benzyl p-hydroxybenzoate and 6.4 g of oxalic acid dichloride to yield di(p-benzyloxycarbonylphenyl)oxalate, m.p. 106°–108° C., as white crystals.

EXAMPLE 13

Into 350 ml four-neck flask equipped with a dropping funnel, a thermometer and a calcium chloride tube are charged 19.4 g of n-butyl p-hydroxybenzoate, 7.9 g of pyridine and 150 ml of ethylether. A solution of 7.8 g of succinic acid dichloride in 20 ml of ethylether is added dropwise to the mixture with stirring while retaining the mixture at 0°–5° C. over 30 minutes. After addition, the mixture is further allowed to react at room temperature for five hours. Thereafter the resulting reaction solution is washed with 200 ml of 1N hydrochloric acid, with 200 ml of water, then with 200 ml of 1% sodium hydroxide solution, and finally with 200 ml of water, and the ether layer is distilled off. The residue is recrystallized from methanol five times, m.p. 70°–71° C., as white crystals.

EXAMPLE 14

Into 300 ml four-neck flask equipped with a dropping funnel, a thermometer, a calcium chloride tube are charged 19.4 g of n-butyl p-hydroxybenzoate, 7.9 g of pyridine and 150 ml of ethylether. A solution of 6.4 g of oxalic acid dichloride in 20 ml of ethylether is added dropwise to the mixture with stirring while retaining the mixture at 0°–5° C. over 30 minutes. After addition, the mixture is further allowed to react at room temperature for five hours. Thereafter the resulting crystals are filtrated, washed with water and recrystallized from toluene to yield di(p-n-butyloxycarbonylphenyl)oxalate, m.p. 100.5°–101.5° C., as white crystals.

EXAMPLE 15

Into 300 ml four-neck flask equipped with a dropping funnel, a thermometer, a calcium chloride tube are charged 25 g of 2-ethylhexyl p-hydroxybenzoate, 7.9 g of pyridine and 150 ml of ethylether. A solution of 12 g of sebacic acid dichloride in 20 ml of ethylether is added dropwise to the mixture with stirring while retaining the mixture at 0°–5° C. over 30 minutes. After addition, the mixture is allowed to react at room temperature for five hours. Thereafter the resulting reaction solution is washed with 200 ml of 1N hydrochloric acid and then with 200 ml of water, and the solvent in the ether layer is distilled off. The residue is purified by column chromatography to yield oily di(p-2-ethylhexyloxyphenyl)sebacate.

What is claimed is:

1. An alkanedicarboxylic diester compound represented by the formula:

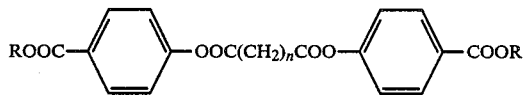

wherein n is an integer of 0–8 and R is benzyl group.

* * * * *